(12) United States Patent
Cronau et al.

(10) Patent No.: US 11,070,965 B2
(45) Date of Patent: Jul. 20, 2021

(54) METHOD AND SYSTEM FOR LINKING DEVICES

(71) Applicant: SPD SWISS PRECISION DIAGNOSTICS GMBH, Geneva (CH)

(72) Inventors: Steven Thomas Cronau, Geneva (CH); Stephen Paul Sharrock, Geneva (CH)

(73) Assignee: SPD SWISS PRECISION DIAGNOSTICS GMBH, Geuena (CH)

( * ) Notice: Subject to any disclaimer, the term of this patent is extended or adjusted under 35 U.S.C. 154(b) by 0 days.

(21) Appl. No.: 16/636,287

(22) PCT Filed: Aug. 3, 2018

(86) PCT No.: PCT/EP2018/071178
§ 371 (c)(1),
(2) Date: Feb. 3, 2020

(87) PCT Pub. No.: WO2019/025609
PCT Pub. Date: Feb. 7, 2019

(65) Prior Publication Data
US 2020/0162873 A1 May 21, 2020

(30) Foreign Application Priority Data
Aug. 4, 2017 (GB) .................... 1712566

(51) Int. Cl.
*H04W 4/80* (2018.01)
*H04W 4/38* (2018.01)
(Continued)

(52) U.S. Cl.
CPC ............. *H04W 4/80* (2018.02); *G01N 33/76* (2013.01); *H04L 67/306* (2013.01); *H04W 4/38* (2018.02)

(58) Field of Classification Search
CPC ................. H04L 67/306; H04W 4/80
See application file for complete search history.

(56) References Cited

U.S. PATENT DOCUMENTS

| 7,174,187 B1* | 2/2007 | Ngan | ............... H04W 88/06 455/552.1 |
| 2004/0044774 A1* | 3/2004 | Mangalik | ............ H04L 67/2819 709/227 |

(Continued)

FOREIGN PATENT DOCUMENTS

| EP | 2661144 | 6/2013 |
| WO | 2017/161285 | 9/2017 |

OTHER PUBLICATIONS

The International Search Report (ISR) with Written Opinion for PCT/EP2018/071178 dated Oct. 10, 2018, pp. 1-10.
(Continued)

*Primary Examiner* — Hsinchun Liao
(74) *Attorney, Agent, or Firm* — McDonnell Boehnen Hulbert & Berghoff LLP

(57) ABSTRACT

A method of linking a first device to a second device, the first device comprising a wireless communication means having a unique address associated therewith, the first device further comprising a display arranged to display a set of indicators, one of the first device or the second device having a unique identity stored thereon, the method comprising: broadcasting, from the first device, the unique address; determining, by the first device, whether one or more indicators from the set of indicators correspond to at least a portion of the unique address based on a first mapping displaying the corresponding one or more indicators; if an input selects at least one indicator from the set of indicators, determining whether the selected at least one indicator corresponds to the portion of the unique address based on a second mapping; and transmitting the unique identity between the devices.

17 Claims, 11 Drawing Sheets

(51) Int. Cl.
*G01N 33/76* (2006.01)
*H04L 29/08* (2006.01)

(56) References Cited

U.S. PATENT DOCUMENTS

| | | |
|---|---|---|
| 2007/0251997 A1 | 11/2007 | Brown et al. |
| 2010/0107092 A1* | 4/2010 | Kindberg ............ G06K 7/10475 |
| | | 715/760 |
| 2012/0256738 A1* | 10/2012 | Egawa .................. G06F 13/385 |
| | | 340/286.02 |
| 2014/0244782 A1* | 8/2014 | Beaurepaire ............ H04W 4/21 |
| | | 709/217 |
| 2014/0254466 A1 | 9/2014 | Wurster et al. |
| 2015/0282224 A1 | 10/2015 | McRae et al. |
| 2015/0301031 A1 | 10/2015 | Zin et al. |
| 2016/0066894 A1 | 3/2016 | Barton-Sweeney |
| 2016/0338117 A1 | 11/2016 | Pandit et al. |
| 2017/0178493 A1 | 6/2017 | You et al. |

OTHER PUBLICATIONS

Search Report under Section 17 for Application No. GB1712566.7 dated Jan. 11, 2018, pp. 1-4.

\* cited by examiner

Fig. 7

| MAC Address Bit | Bit State | |
| --- | --- | --- |
| | Bit SET (1) | Bit CLEAR (0) |
| 0 (least significant bit) | Book | No Book (blank) |
| 1 | Stick | No Stick (blank) |
| 2 | Eyes and Mouth | No Eyes and Mouth (blank) |
| 3 | Star | No Star (blank) |

METHOD AND SYSTEM FOR LINKING DEVICES

CROSS-REFERENCE TO RELATED APPLICATIONS

This application is a U.S. National Stage application of International Patent Application PCT/EP2018/071178, filed Aug. 3, 2018, which claims the benefit of priority of U.K. Patent Application GB1712566.7, filed Aug. 4, 2017.

FIELD

The disclosure relates to a method and system for linking devices. In particular, the invention relates to a method and system for linking a first device to a second device, the first device comprising a wireless communication means.

BACKGROUND

Devices for the determination of analytes present in a sample such as urine, are widely available over the counter and are common in professional use. Such devices are designed to be simple to use and for example provide information relating to ovulation, pregnancy and menopause. Currently available ovulation test devices include those that are intended for home use being designed to be used by women who are either trying to become pregnant or are deliberately avoiding pregnancy. Such products may provide an indication of a woman's fertility throughout the course of the woman's menstrual cycle or indicate a woman's fertility during selected times of her menstrual cycle. Typically, these test devices comprise a specific area(s) where biochemical reactions with the analyte(s) of interest take place, thereby allowing the identification and/or quantification of the analyte(s) present in the sample from which the test result is determined. In certain 'visual test devices', the user may examine the specific area(s) and interpret the test result themselves, however in other 'digital test devices' a detection means may be used to interpret the specific area(s) and output the test result on a display located on or within the test device. Digital test devices can incorporate a power source (battery) and electronic circuitry to drive the detection means as well as a display and are typically designed to be disposable, having a defined battery capacity which has to be carefully balanced to ensure adequate longevity of the reading device. Ovulation tests therefore identify those days in a woman's cycle on which intercourse is most likely to lead to conception.

One known product defines three phases of fertility through urine hormone measurement. These phases of fertility may be termed "low" (lower chance of conceiving), "high" (increased chance of conceiving), which is determined by detecting a rise in the level of Estrone-3-Glucuronide (E3G), and "peak" (higher chance of conceiving), which provides an early warning of impending ovulation through detection of the luteinising hormone (LH) surge. Such a surge typically precedes ovulation by 24-36 hours. The results, in terms of low, high or peak, are displayed on a display of the digital ovulation test device to provide such information to a user.

The determination of ovulation typically requires testing to be performed on a daily basis, the measurements and results from previous days' testing being used in an algorithm to define the fertile state on the next testing occasion. The detection of hormones may be made through the combination of the ovulation test device (which acts as a reader) and a number of disposable test sticks, the test sticks typically incorporating the specific area(s) where biochemical reactions with the analyte(s) take place. The specific area(s) where biochemical reactions take place may be encompassed within a detection region. The specific area(s) may take the form of a line(s) known as a test line(s) or assay test line(s). A test stick may also be referred to as a test strip, and these terms may be used interchangeably.

To perform a test, the user inserts a test stick into the reader and then applies a sample, which is usually urine. The user may apply the sample to the test stick as a first step and then insert the test stick into the reader. Alternatively, the test stick may already be placed into the reader before the application of a sample. In the instance where the hormones LH and E3G are being measured, the test stick incorporates two immunochromatographic assays that develop test lines on the test stick, the intensity of which is relative to the concentration of each analyte in the sample. The reader interprets the intensity of the test lines by virtue of the detection means, for example by illuminating the test stick and detecting a reflection from the test stick. Alternatively, a transmission of light through the test stick may be used. Values based on the changes in reflection or transmission of light due to the intensity of the assay lines and values derived from previous tests may be applied to an algorithm to determine a state of fertility. This result is passed to the user in the form of a qualitative result displayed on a display of the device. The result reflects the intended use of the product, i.e. to determine a fertility state.

Since test devices are often designed to be disposable after a defined period of use, any improvement to the functionality of the test device is heavily constrained by cost. One example functionality that is desirable in test devices can be found in certain devices which also have wireless data connectivity in order to send ovulation, fertility or other data to an external device such as a mobile phone or a computer. Such a device may be a digital ovulation test device. Security and other connectivity issues arise due to the wireless transmission of data. A connection step is required to wirelessly connect the external device to the test device such that data can be transmitted privately. Typically, this is achieved by providing a printed identification on the test device, such as a device name or code, as well as a password or key code. The external device can display the identification in a list of wireless devices detected by the external device. On selecting the identification matching that of the test device, the external device and test device are connected via manual input of the password or key code. On successful input, data can be transferred between the two devices.

A drawback of using a printed identification and password is that this increases the costs of the test device, as such information must be added to the exterior of the device to be visible by a user. Digital ovulation test devices are typically designed for limited uses and are disposable. As such, reducing production costs of such devices is particularly desirable.

SUMMARY

An invention is set out in the claims.

According to an aspect, a method of linking a first device to a second device is provided. The first device comprises a wireless communication means having a unique address associated therewith. The first device further comprises a display arranged to display a set of indicators, one of the first device or the second device having a unique identity stored thereon. The method comprises: broadcasting, from the first device, the unique address; determining, by the first device, whether one or more indicators from the set of indicators correspond to at least a portion of the unique address based on a first mapping and, if one or more indicators correspond, displaying, on the display, the corresponding one or more indicators; detecting, by a second device, the unique address broadcast by the first device; displaying, on the second device, the set of indicators, the second device being arranged to receive an input from a user; wherein, if the input selects at least one indicator from the set of indicators, determining whether the selected at least one indicator corresponds to the portion of the unique address based on a second mapping; and wherein, if the selected at least one indicator corresponds to the portion of the unique address, transmitting the unique identity between the first device and the second device.

Optionally, the unique identity is shared between the first and second devices.

Optionally, the second device has the unique identity stored thereon, the unique identity being associated with a user account.

Optionally, the first device has the unique identity stored thereon.

Optionally, the first and second mapping each comprises a list of indicators, each indicator associated with an element of the unique address.

Optionally, the first mapping and the second mapping are the same.

Optionally, at least a portion of the first mapping and the second mapping is the same.

Optionally, the second mapping comprises the first mapping and at least one additional mapping.

Optionally, when the first device is broadcasting, the first device is arranged to display a wireless indicator from the set of indicators, the wireless indicator indicating that the wireless communication means is active.

Optionally, when the first device is broadcasting, the first device is arranged to display a wireless indicator from the set of indicators, the wireless indicator indicating that the wireless communication means is active, and wherein the at least one additional mapping associates the wireless indicator with an element of the unique address.

Optionally, the first mapping is stored in a memory of the first device.

Optionally, the second mapping is stored in a memory of the second device.

Optionally, the display is only arranged to display indicators from the set of indicators.

Optionally, the indicators are symbols, shapes, icons, alphanumeric or images.

Optionally, the method further comprises the step of receiving, at the first device, the unique identity and storing the unique identity in a memory of the first device.

Optionally, the method further comprises the step of, receiving, at the second device, the unique identity and storing the unique identity in a memory of the second device.

Optionally, the step of receiving an input comprises receiving the input on a touchscreen or keypad of the second device.

Optionally, the wireless communication means comprises Bluetooth® or Bluetooth® Low Energy (BLE).

Optionally, the unique address is a MAC address.

Optionally, the portion is a number of bits of the MAC address.

Optionally, the number of bits is the last four bits.

Optionally, the first and second mapping each comprises a list of indicators, each indicator associated with at least one bit of the MAC address.

Optionally, each indicator is associated with a bit state of at least one bit of the MAC address.

Optionally, the first device is arranged to operate in a first mode and a second mode, the first device displaying the indicators in a first indicator state while in the first mode and in a second indicator state while in the second mode, the second mode comprising the previously mentioned step of displaying, on the display, the corresponding one or more indicators.

Optionally, the first indicator state is different from the second indicator state.

Optionally, the first indicator state is a static state.

Optionally, the second indicator state is a flashing state.

Optionally, the first device is a result reading device, such as an ovulation test device or a pregnancy test device.

Optionally, the set of indicators comprises indicators indicative of one or more test results.

Optionally, the set of indicators further comprises an indicator to indicate that the wireless communication means is active.

Optionally, the result reading device is arranged to operate in a testing mode and a linking mode, the result reading device displaying the indicators in a first indicator state in the testing mode and in a second indicator state in the linking mode, the linking mode comprising the step in claim 1 of displaying, on the display, the corresponding one or more indicators.

Optionally, the testing mode comprises displaying one or more indicators indicative of a test result on the display.

Optionally, the result reading device is arranged to receive a test stick comprising a detection region, and wherein the first device comprises a detection means arranged to detect the result of a test by analysing the detection region.

Optionally, the unique identity is a code.

Optionally, the second device is a mobile wireless communications device.

Optionally, the unique address is manufacturer specific data.

Optionally, subsequent transmittance of data between the first and second device requires a matching step to confirm that the unique identity of the first device matches the unique identity of the second device.

Optionally, the first device is disposable.

According to a second aspect, there is provided a system for linking a first device to a second device.

According to a third aspect, there is provided a device for displaying a linking code.

According to a fourth aspect, there is provided a device for linking with an external device.

BRIEF DESCRIPTION OF FIGURES

Embodiments of the invention will now be described, by way of example, with reference to the following drawings, of which:

FIG. 7 shows an embodiment of a mapping between MAC address bits and indicators;

Throughout the description and drawings, like reference numerals refer to like parts.

DETAILED DESCRIPTION

Figure 1:
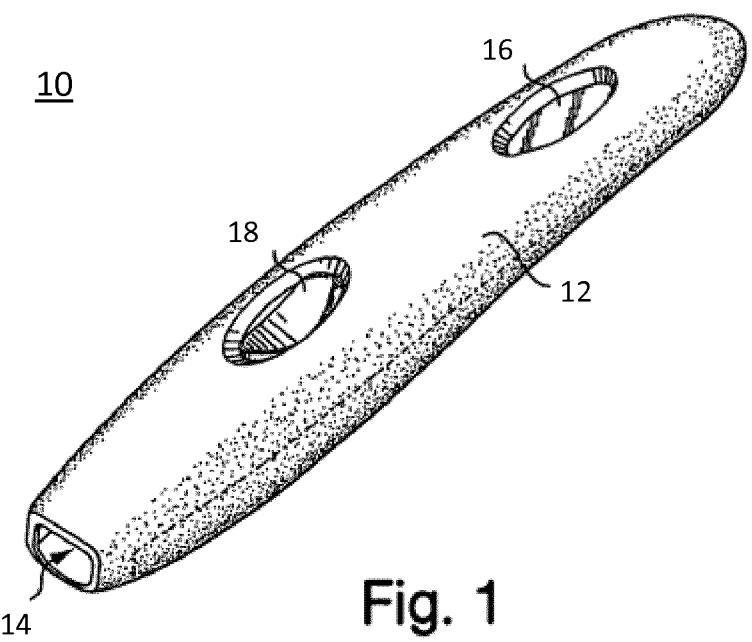
FIG. 1 shows a perspective view of a known assay result reading device.

Disclosed herein is a method and system for linking a first device to a second device. Particularly, the disclosed method and system is suited for linking a testing device to an external device, the testing device and the external device having corresponding wireless communication means. The term "testing device" means any device that performs a test and outputs or displays a result. For example, the testing device could be an assay result reading device that detects biochemical content of a sample and outputs a result. The assay result reading device may be a digital ovulation test device for in-home use by a woman to determine a relative state of fertility at a certain point in the woman's cycle.

In order to aid understanding of the invention, an example system will first be described. Such a system uses an assay result reading device and a separate test stick. The determination of fertility based on the assay result reading device and the test stick is achieved optically, as described in EP1484601B1. As an example, the assay result reading device is arranged to receive the test stick and thereafter provide an indication of a woman's fertility based on an optical analysis of a detection region of the test stick. The detection region of the test stick may also be termed a test strip. The assay result reading device comprises a light source arranged to illuminate a test zone of the detection region when the test stick is inserted and retained within the device, and a photodetector to detect the reflection of light from the detection region, or the transmission of light through the detection region.

The test zone is an area of the detection region which includes an area in which an assay line may develop. The assay result reading device may have more than one light source, for example first, second and third light sources. The detection region of the test stick may comprise additional zones. For example, additional test zones may be present in which the same or another analyte is determined. In some instances at least one additional zone known as a control zone may be present within the detection region of the test stick. The relative position of the test and control zones can be varied, with the control zone present either upstream or downstream of any test zone. In this example, having three light sources, each light source is arranged to illuminate a corresponding first, second and third zone. Each zone is a portion of the total area provided by the detection region of the test stick.

Each test zone may serve a different purpose, measuring the same or different analyte in the sample. In addition the detection region may include areas or zones where there is no analyte measurement taking place, and these areas or zones may be interrogated by a measurement means to provide a reference zone for the detection region. The reference produced may be used to compensate for variations in the background colouration of the detection region which may vary between test sticks run with samples having varying colours, for example urine samples which can be concentrated due to dehydration for example where the sample is darker. Variations in running of the test stick can produce different degrees and variations in the rate of release of dried reagents, typically direct particulate labels such as dyed latex or colloidal gold sol, thereby producing variations in colouration of the background of the detection region. The reference zone can be used to compensate and account for such variations. For example, the first zone of the detection region may be a test zone, the second zone may be a reference zone, and the third zone may be a control zone. The test and control zones may be of any shape and size, and typically these are perpendicular lines relative to the length of the detection region/test strip.

The test zone is the zone in which accumulation or deposition of a label takes place, such as a particulate coloured binding agent, in response to the presence or absence of a particular analyte. For example, one analyte may cause a coloured line to appear in the test zone, such that a portion of the light reflected off or passing through this zone is absorbed. Other test devices may use alternative label and appropriate measurement means, for example electrochemical determination or use of fluorescent labels generating a fluorescent signal.

The control zone is the zone that acts as an experimental control. In this zone, an optical signal is formed irrespective of the presence or absence of the analyte of interest. This is to show that the procedure has been correctly performed and/or that the binding reagents are functional.

Calibration of the reading device may be performed in various ways, including calibration at the point of manufacture. Further calibration may take place during use of the test device to characterise the particular test stick being used. Calibration measurements may take readings from all or some of the zones within the detection region. All or some of the zones in the detection region may be used to validate the flow along the test strip. The reference zone may be used as a means to compensate for background signal resident on the test strip when it has been wetted with sample. An example calibration method is described in EP1484601B1, paragraphs [0041]-[0043].

In the case that only a single light source and only a single photodetector are used, the detection region may not be divided into different zones, and the entire detection region may serve the same function as the test zone. Alternatively, the test zone may be a defined region within the detection region. In the case that three light sources are used and the detection region is divided into three zones, the assay result reading device may comprise first and second photodetectors. The first photodetector is associated with the first light source, and may be located adjacent thereto. The first photodetector is arranged to detect light emanating from the first zone of the detection region. However, the first photodetector is so positioned as to detect some of the light emanating from the second zone.

The second photodetector is associated with the third light source, and may be located adjacent thereto. The second photodetector is arranged to detect light emanating from the third zone of the test strip. However, as for the first photodetector, the second photodetector is so positioned as to detect some of the light emanating from the second zone. In the case that the assay result reading device comprises a plurality of light sources, optical baffles may be provided between the light sources so as to help constrain the light from each light source to its respective zone, in combination with a microprocessor used to control which light sources are active in relation to specific photodetectors. Such an arrangement allows for the determination of results from three zones within the detection region by using two photodetectors, and presents a cost saving both in terms of component parts as well as simplifying manufacturing complexity.

It is also possible to use a plurality of light sources, each illuminating separate zones within the detection region, in conjunction with a single photodiode to detect light from each zone. In this case, the microprocessor controls the activation of the light sources as well as the detection by the photodetectors. Again, optical baffles are used to help constrain the light from each light source to its respective zone.

Figure 2:
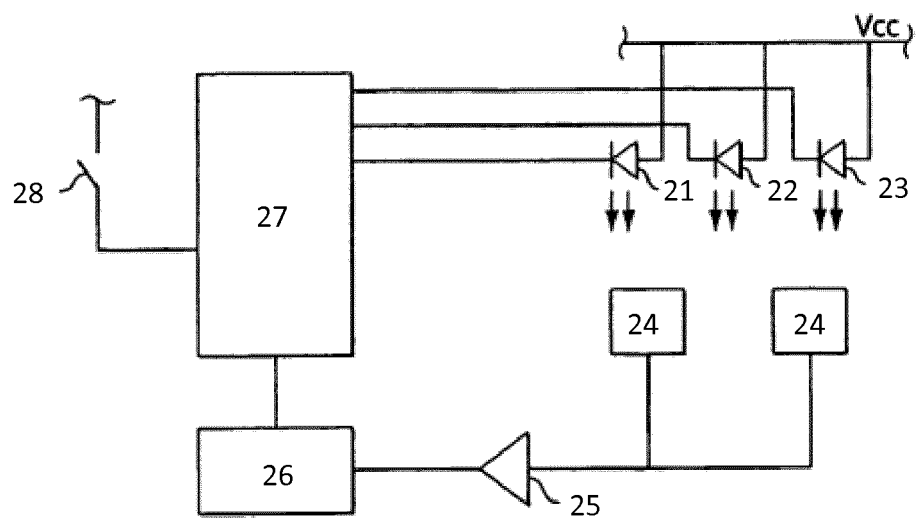
FIG. 2 shows example components located within the housing of the device of FIG. 1.
Figure 3:
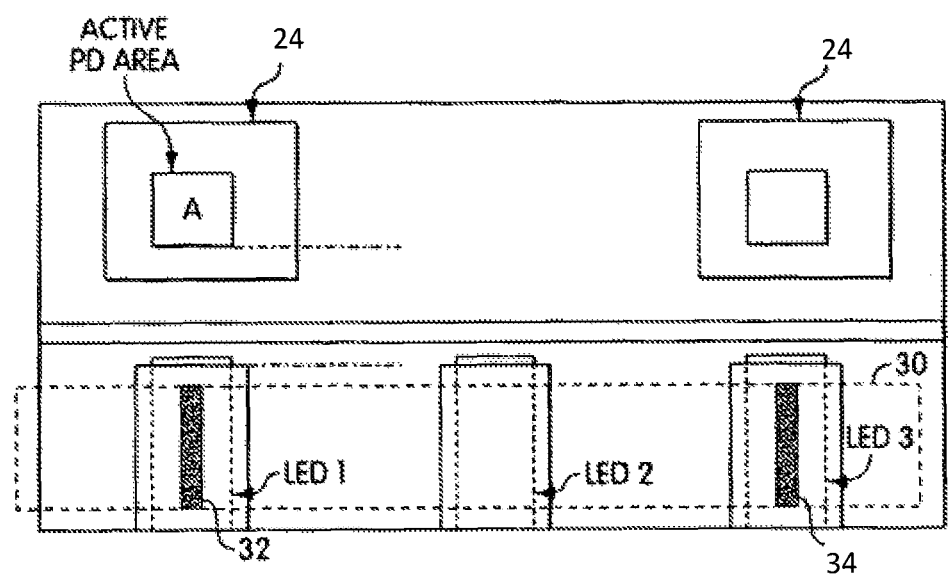
FIG. 3 shows an example arrangement of photodetectors and LEDs of the device of FIG. 1.

FIGS. 1-3 show an example assay result reading device and a test stick useful for understanding the invention. An example assay result reading device 10 is illustrated in FIG. 1. The reading device may be about 12 cm long and about 2 cm wide and is generally finger-shaped, however other dimensions and shapes may of course be used. The device 10 comprises a housing 12 formed from an opaque plastics material. The device has an aperture or insertion opening 14 at one end into which a test stick can be inserted. One face of the device 10 comprises an opening through which a display 16 may be seen. The display 16 can be any kind of conventional display, such as a liquid crystal display. The display 16 is arranged to provide information to a user of the device 10. The device also comprises ejection means 18 for ejecting a test stick from the device 10. The ejection means may be any suitable means, such as a push button arranged to eject a test stick from the device 10. The device 10 may also have an internal stopping abutment to limit insertion of the test stick into the device 10.

The test stick for use with the reading device is a generally conventional lateral flow test stick, for example of the sort disclosed in U.S. Pat. Nos. 6,156,271, 5,504,013, EP 728309, or EP 782707. In particular, the test stick having a strip of porous solid phase material as disclosed from page 6 line 24 to page 8 line 8 of EP291194B1 may be used. The test stick is sized and shaped to be insertable into the device 10, through the opening 14. The test stick is conventionally an elongated strip shape, however other shapes may be used.

FIG. 2 shows example components located within the housing 12 of the device 10. As mentioned, the device 10 may only have a single LED and a single photodetector, however the device shown in FIG. 2 has three LEDs and two photodetectors. The device 10 of FIG. 2 comprises a first LED 21, a second LED 22 and a third LED 23. When a test stick is fully inserted into the device 10 so as to abut the switch, each LED is aligned with the respective one or more zones of the detection region of the test stick. Two photodiodes 24 operate in the conventional manner: light is detected after reflection or transmission from each zone to generate a current, the magnitude of the current being proportional to the amount of light incident upon the photodiodes 24. In this example, the current generated is converted to a digital value by the microcontroller. Various other ways of converting the incident light exposed to the photodiodes are known in the art. In order to illuminate only one of the zones (primarily) at a given time, the microcontroller 27 switches the LEDs on individually, one at a time. The signals generated by reflected or transmitted light can therefore be attributed to a specific zone with the knowledge of when and which LED was switched on.

FIG. 2 also shows a switch 28. This switch 28 is an internal mechanical switch 28 located within the housing 12 of the device 10. Insertion of the test stick into the device 10 causes an abutment and activation of the switch 28. The activation of this switch "wakes" the device 10 from a "dormant" state into an active state by activating the microcontroller 27. The switch may additionally be positioned to perform the function of the internal stopping abutment to restrict the lateral movement of the test stick within the housing 12, meaning a separate stopping abutment is not provided. The device 10 also includes a power source for providing power to these components. Such a power source may be a battery, such as a coin cell battery for example.

An example method of using the assay result reading device 10 and a test stick to conduct an assay will now be described. At one end of the test stick is a sample receiving portion for receiving a sample to be analysed by the device 10. The sample receiving portion is typically located at an opposite end of the test stick to the end that would be inserted into the device 10. The sample receiving portion of the test stick is exposed to a liquid sample, typically urine, either before or after insertion of the test stick into the device. The exposure may be by placing the end of the test stick having the sample receiving portion into a urine sample pre-collected in a container or a urine stream from an individual for a duration of time, such as 5 seconds.

The device 10 then detects the intensity of light emanating from the detection region of the test stick. In other words, the device 10 detects the intensity of light reflected by or transmitted through the detection region of the test stick. Although reflected light is primarily referred to below, it is to be understood that the one or more LEDs and the one or more corresponding photodetectors may be located on opposite sides of the device 10. In this case, transmitted light is detected and the detection region must be transparent or translucent to allow light to pass from an LED, through the detection region and onto a photodetector.

In the case of the detection of reflected light, reflected light intensity from one or more of the zones of the detection region is then measured using the one or more photodetectors. The detection process may take place at a predetermined time interval following insertion of the test strip into the device 10, or may begin immediately. Measurements of light intensity may be taken multiple times, and averaging may be used to improve accuracy. Multiple measurements of light intensity may be taken over a period of time to provide a kinetic change of the light emanating from any of the zones to profile how the signal changes from any of the zones as a function of time. The LEDs used within the reader can be selected to emit a particular wavelength of light which is largely absorbed by the label of choice as it collects at the zones present in the detection region in an analyte dependent manner.

FIG. 3 shows an example arrangement of how three LEDs may be arranged with two photodetectors. Each photodetector has an active area (A) that is sensitive to light. The optical setup is arranged such that the centre lines of LEDs 1 and 3 correspond to the centre lines of the photodetectors 24. The LEDs and photodetectors shown in FIG. 3 may be located within an area of about 1 square cm. FIG. 3 also shows a detection region 30 of a test stick located above the three LEDs. The detection region 30 shown has a detection zone 32 and a control zone 34 which, when the test stick is inserted into the device 10, are located above LED 1 and LED 3 respectively.

The detection region 30 may be a known test strip comprising a layer of a porous carrier, such as nitrocellulose, which may be adhered or cast onto a layer of plastic, such as MYLAR <®>. An additional plastic cover may be placed or adhered to the surface of the nitrocellulose in totality or in part. The plastic layer of the detection region 30 that is proximal to the one or more LEDs must be transparent or translucent to allow light through. In the case that the one or more LEDs and the one or more photodetectors are located on the same side of the device 10, and therefore on the same side of the detection region 30 when the test stick is in the device 10, the plastic layer distal to the one or more LEDs must be capable of reflecting light. Preferably, the distal plastic layer is white to increase contrast and hence the signal to noise ratio. In the case that the one or more LEDs are located on an opposite side of the device 10 to the one or more photodetectors, i.e. the LED and photodetector are located on either side of the detection region 30, the plastic layers must both be transparent or translucent such that light can pass through the detection region 30.

It can be seen from the above description of FIGS. 1-3 that a known assay result reading device 10 is able to perform a test by receiving a test stick having a detection region 30, analysing the detection region 30 optically, and outputting a result on the display 16 of the device 10. The assay result reading device analyses the assay test lines that appear in the detection region and interprets the intensity of these assay test lines based on detecting the attenuation or transmission of light from the LEDs. One or more values indicative of the attenuation or transmission may be stored in a memory of the device. Measurement values from the test just completed are applied to an algorithm to determine a state of fertility. When performing additional tests, the results from the test just completed may be used in combination with all or some of the previous tests in an algorithm to determine the current state of fertility. Once a state of fertility is determined, a visual indication of the state of fertility is displayed on the display 16.

For example, a "peak" fertility state, representing a maximum fertility, may be displayed as a symbol such as a smiley face. Conversely, a "low" fertility state, representing a minimum fertility, may be displayed as a different symbol, such as a sad face or an empty circle. In this manner, the user is provided with an easily interpreted indication of their current fertility state. Additional or different fertility states and additional or different visual indicators of fertility may of course be used.

The above described performance of a test and displaying the test result may be regarded as a first mode of operation of the testing device. Such a first mode may be termed a testing mode.

Figure 4:
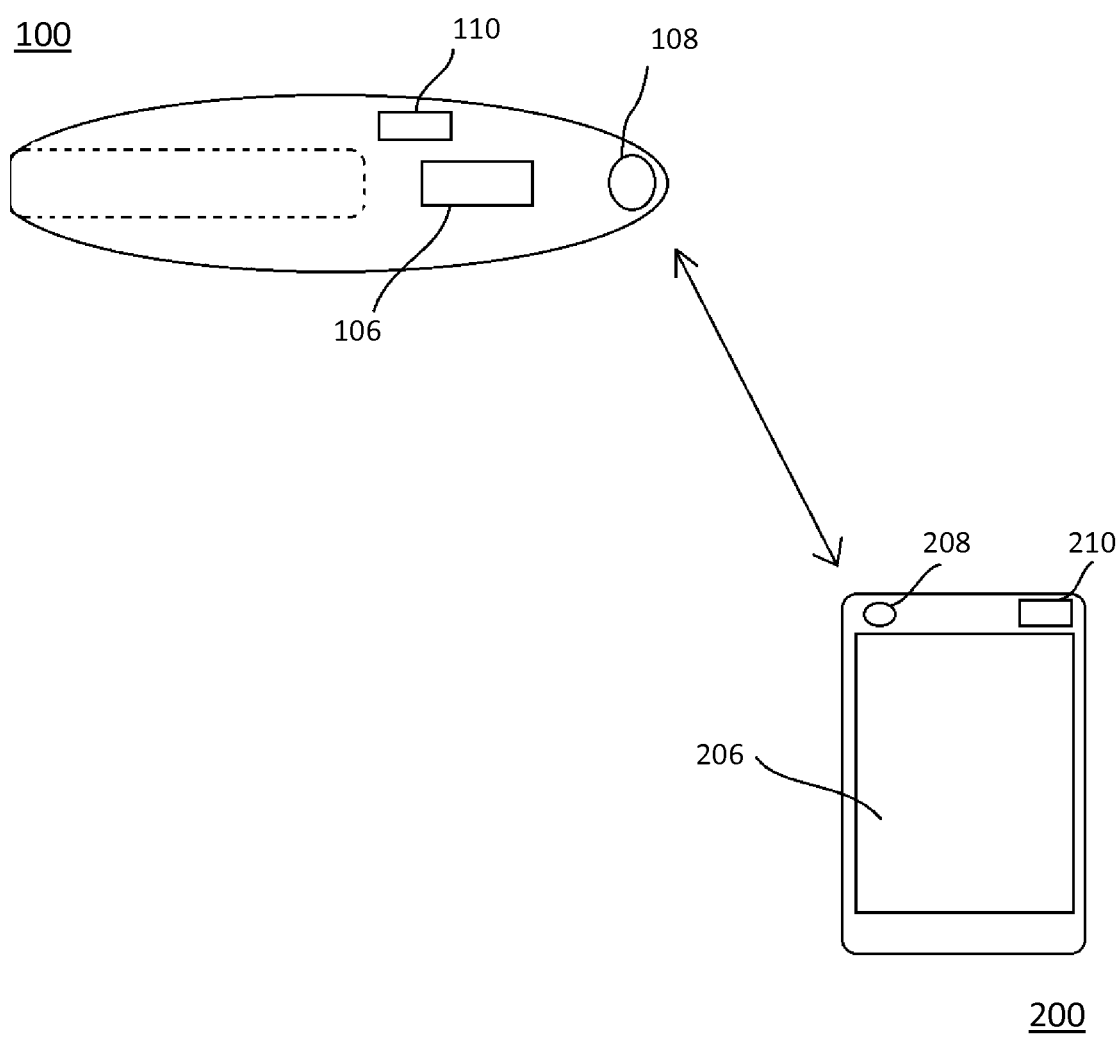
FIG. 4 shows a testing device and an external device in accordance with an embodiment.

An embodiment of a testing device 100 and an external device 200 will now be described in relation to FIG. 4. The testing device 100 may be the same type as the assay result reading device 10 of FIG. 1, or may be a different type of device that is able to indicate the results of a test. Indeed, a disposable testing device is particularly suited to being the testing device 100. The testing device 100 comprises a display 106 for providing a visual indication of a test result. In the case of the testing device 100 being the same type as the assay result reading device 10, the display 106 is the display 16. The device 100 further comprises wireless communication means 108.

The wireless communication means 108 may be any means of wirelessly communicating data, for example Bluetooth®. In particular, Bluetooth® Low Energy (BLE) may be used to minimise the impact on battery life of the device 100. As the skilled person would understand, other wireless data communication means may be used, such as ZigBee, Z-Wave, WiFi, 2G, 3G, 4G, NFC, RFID, ANT, among others. While Bluetooth® is referred to specifically, the functionality described below applies to other types of wireless data communication means.

Figure 5A:
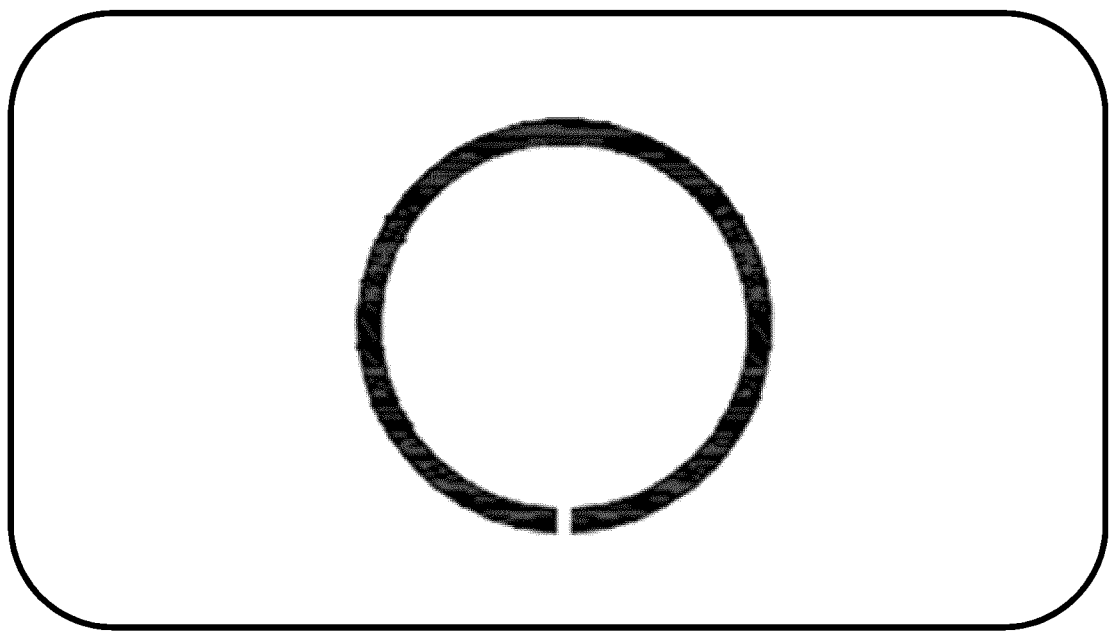
FIG. 5a shows an example indicator to display a "low" fertility result on the testing device.
Figure 5B:
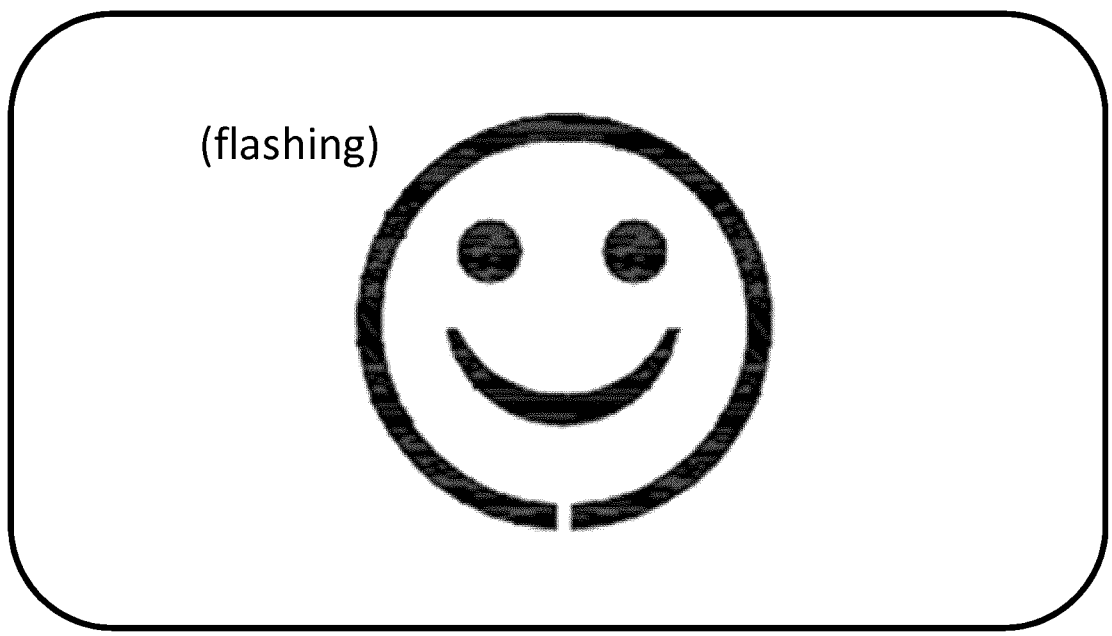
FIG. 5b shows an example indicator to display a "high" fertility result on the testing device.
Figure 5C:
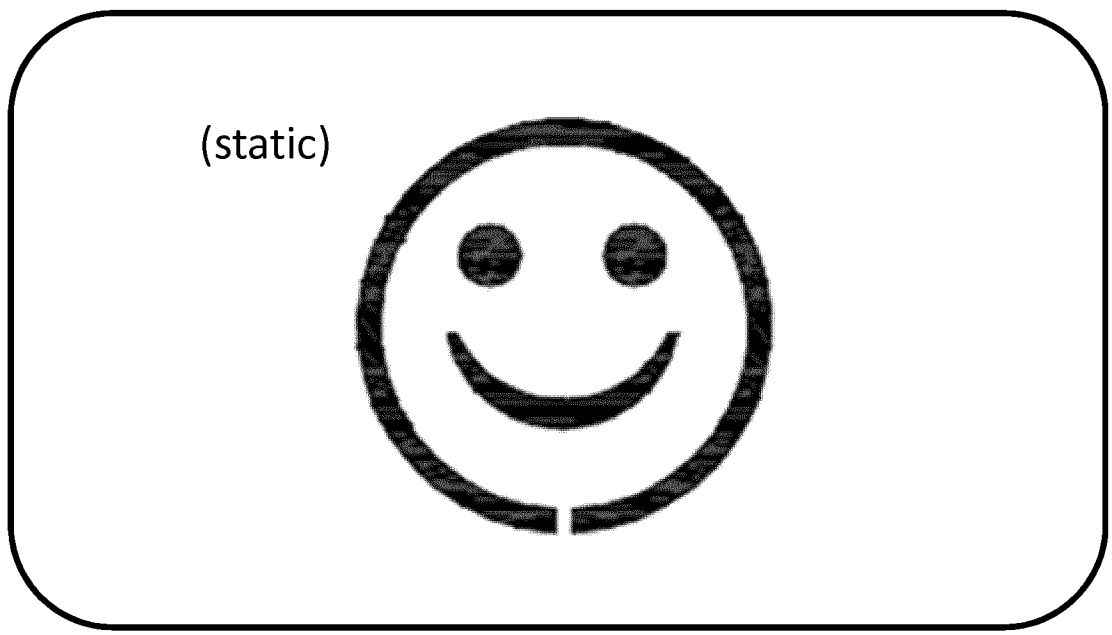
FIG. 5c shows an example indicator to display a "peak" fertility result on the testing device.

The display 106 may be a simple LCD or other display that is only capable of displaying a limited number of indicators. The word "indicator" means an image, symbol, icon, alphanumeric or other element that can be represented graphically. During a first mode of operation, i.e. the testing mode or "normal" use of the testing device 100, only a limited number of indicators are required to convey the necessary test result information to a user and therefore the display 106 is only capable of displaying a limited number of indicators. In the example of the device 100 being the same type as the assay result reading device 10, during normal use the testing device 100 may display indicators relating to: low fertility, high fertility, peak fertility, low power, wireless transmission activated and the like. These specific indicators are merely examples in the case that the testing device 100 tests for fertility, however different indicators may be used if the testing device 100 is arranged to perform a different test. As the testing device 100 is only arranged to display these certain indicators during use, a simple display 106 may be used that is only capable or only arranged to display a limited set of indicators. By using a simple display, costs are saved and complexity is reduced without compromising the effectiveness of the testing device 100. FIGS. 5a, 5b and 5c show example indicators that correspond to low fertility, high fertility and peak fertility respectively.

The following further details are an example in the case that the testing device 100 is the same type as the assay result reading device 10. However, as would be understood, the testing device 100 could be any device that is able to indicate the results of a test. During the testing mode, i.e. "normal" use, the following procedure may occur: a user inserts a test stick into the testing device 100 and applies a urine sample to the test stick. Alternatively, the urine sample may be applied to the test stick first, and the test stick then inserted into the testing device 100. The testing device 100 then proceeds to analyse the test stick in the manner previously described in relation to the assay result reading device 10. Optionally, while the testing device 100 is analysing the test strip, an indicator may be displayed on the display 106. This indicator may be a flashing egg timer or a flashing test stick, for example, indicating that analysis of the test results is in progress. After the testing device 100 has analysed the test strip, the testing device 100 then displays the result of the analysis on the display 106. If, for example, the result is peak fertility, an indicator being a smiling face image or symbol may be displayed statically. If, on the other hand, the result is low fertility, an indicator being circular ring image or symbol may be displayed statically. Optionally, if at any time the testing device 100 is at low power, an indicator may be displayed such as a flashing battery image or symbol.

As would be understood, the specific indicators are for example purposes only. The testing device 100 may display more or fewer indicators, and may display indicators at different times. Additionally, certain indicators may flash at one rate or a variety of different rates, be static, or have another indicator state that is predefined to correspond to a specific result or event. Each event therefore has a corresponding, predefined indicator or indicators that would be displayed in a predefined indicator state. The testing device 100 is arranged to display a limited number of indicators in a limited number of indicator states (e.g. flashing, static or similar), a specific indicator and indicator state being associated with a specific result or event. Low cost disposable testing devices, such as the testing device 100, are designed in a cost effective manner which means the size of the display is kept to a minimum (typically LCD displays are used). This in turn limits the number of indicators that can be displayed. As such, the display 106 is beneficially arranged to use the same indicators as part of both a testing procedure and an identification process.

Figure 6:
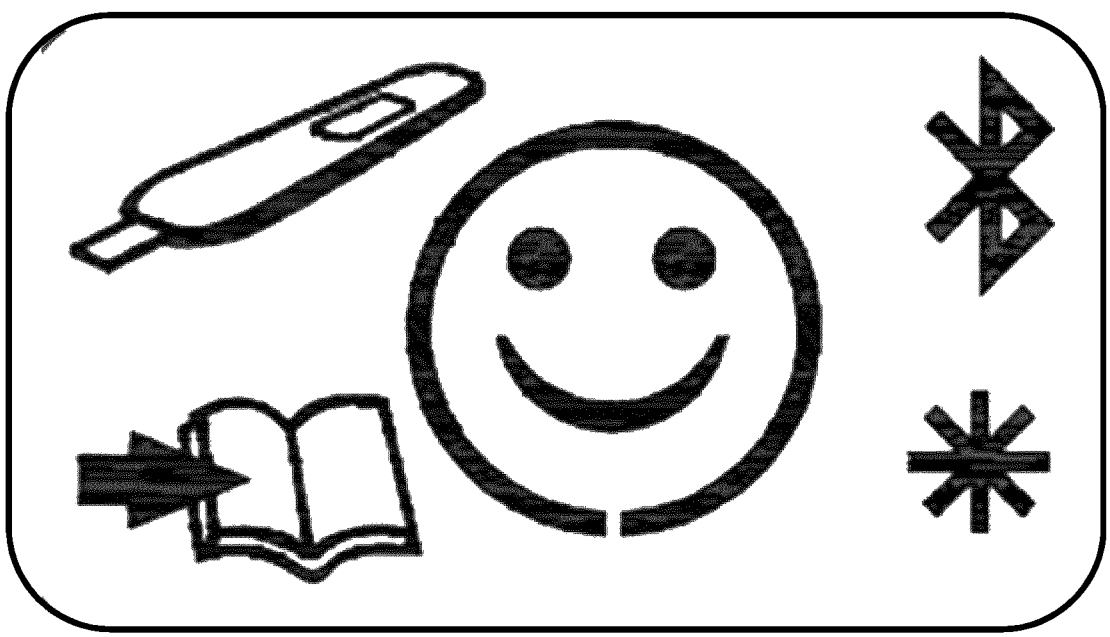
FIG. 6 shows an embodiment of a set of indicators displayable by the testing device.

During the testing mode ("normal" use) of the testing device 100, the testing device 100 is arranged to display one or more of the indicators in a predefined indicator state in response to specific events. As explained above, one example event may be detecting peak fertility which results in a smiling face image/symbol being displayed in a static indicator state. FIG. 6 shows an embodiment of a set of indicators displayable by the testing device 100. As can be seen, the set of indicators in this example comprises the following indicators: "stick" (top left), "book" (bottom left), "eyes and mouth" surrounded by "circle" (center), Bluetooth® "B" (top right) and "star" (bottom right). This set of indicators is purely an example, and a completely different set of indicators may be used depending on the requirements of the testing device 100 and the test results to be displayed by the testing device 100.

The wireless communication means 108 has a unique address associated therewith. The unique address serves to distinguish a wireless communication means of one device from a wireless communication means of another device. Such a unique address is typically assigned to a wireless communication means of a device at the point of manufacture. In this way, when two similar devices are transmitting data simultaneously, one device may be distinguished from the other by way of their unique addresses. The unique address of the wireless communication means 108 may be regarded as manufacturer specific data.

The unique address may be any data loaded on to the testing device 100 at manufacture. One example of the unique address is a Media Access Control (MAC) address. However, the unique address may be any other manufacturer specific data that serves as a unique number and/or character string specific to the testing device 100. Although the use of a MAC address is described specifically, this is one example and other unique address types may be used.

A MAC address is represented by a number of bits, such as one of the well-known EUI-48 or EUI-64 identifiers which correspond to 48-bit and 64-bit addresses respectively. The device 100 comprises a memory 110 having a mapping or key. The words mapping and key are interchangeable, and refer to a table or listing for converting a particular bit location and a particular bit state to one or more indicators. The mapping provides a manner of automatically matching specific bits and bit states of the MAC address to specific indicators displayable on the testing device 100. As the testing device 100 is only able to display a limited number of indicators, and for practicality, only limited bits of the MAC address are used for matching. For example, only the last 4 bits of the MAC address may form part of the mapping.

FIG. 7 shows an embodiment of a mapping between each bit of the last 4 bits of the MAC address and the indicators. Such a mapping would be used by the device 100. MAC address bit 0 is known in the art as the least significant bit, which is the last bit of the MAC address. As shown in FIG. 7, if the last 4 bits of the MAC address are in the state 1001 for example, the testing device 100 would display the indicators: "book" and "star". As bits 2 and 3 are "0" in this example, a "blank" would be present in the location of the display 106 that is arranged to display a "stick" indicator and an "eyes and mouth" indicator. In other words, the display 106 does not display any indicator in these locations for this example MAC address.

Optionally, a "B" symbol may also be displayed while the wireless communication means 108 is active. In this way, in the event that the last 4 bits of the MAC address are in the states 0000 (and therefore no indicator would not be present on the display based on the mapping of FIG. 7), the display is not entirely blank. Instead, only the "B" symbol is shown. This is beneficial to avoid confusion that the device 100 has turned off (due to low power, for example).

In an embodiment, while the testing device 100 is in a second, linking mode of operation as discussed below, all of the indicators displayed on the display 106 as a result of the mapping are displayed in a flashing indicator state. Particularly, the indicators may be displayed using a slow flash in which the indicators are "on" or present on the display 106 for 1 second, and then "off" or absent from the display 106 for 1 second (and then repeat). This may be beneficial if the testing device 100 uses indicators in a static state to display test results (first mode of operation), as the different indicator state serves to distinguish indicators associated with a MAC address from indicators associated with a test result. As such, the indicator states associated with the MAC address may be different from the indicator states associated with a test result. In other words, the indicator states used for the second (linking) mode of operation may be different from the indicator states used for the first (testing) mode of operation. The beneficially prevents confusion as the user is able to clearly distinguish indicators relating to the testing mode of operation from indicators relating to the linking mode of operation, based on the differing indicator states.

As the skilled person would understand, the number of bits and the specific indicators used as the mapping is particular to the testing device 100 and the capabilities thereof. Although particular indicators have been shown in FIG. 7, the testing device 100 may be arranged to display a completely different set of indicators, and may use any number of bits of the MAC address. Indeed, any indicator that would be displayed by the testing device 100 in normal operation (testing mode) may be used.

The mapping between the unique address of the wireless communication means 108 and indicators can advantageously be used to link a particular testing device 100 to an external device 200. The external device 200 may be any device capable of wireless communication with the testing device 100, and indeed must therefore have a corresponding wireless communication means 208 able to communicate with the wireless communication means 108. For example, the external device 200 may be a mobile wireless communications device such as a mobile telephone or a tablet, having Bluetooth® functionality.

As well as comprising the wireless communication means 208, the external device 200 comprises a display 206 and a memory 210. The memory 210 also contains a mapping of MAC address bits to indicators. This mapping may be the same as the mapping stored on the device 100 or may include the mapping stored on the device 100 along with additional mapping. For example, the mapping of the external device 200 may include the mapping of the device 100 (FIG. 7), and may also include an additional mapping to account for the case when all the bit states do not correspond to an indicator. Using the mapping of FIG. 7, such a scenario would occur in the case that the last 4 bits of the MAC address are in the states 0000. In this case, the least significant bits all correspond to "blank", and therefore none of those indicators are displayed on the device 100. The additional mapping therefore automatically matches the absence of these indicators to the bit clear state for those bits, i.e. 0000. In an embodiment, the "B" symbol mentioned previously is displayed while the wireless communication means 108 is active. In this case, when the states are 0000 then only the "B" symbol is present on the display 106. The additional mapping may therefore automatically match the presence of only the "B" symbol to the last 4 bits being in the states 0000. In another embodiment, no "B" symbol may be used and the additional mapping may instead automatically match the absence of any indicators to the last 4 bits being in the states 0000.

Conventionally, wireless communication between two devices is established via printing or otherwise fixing a code or number to the side of one of the devices, and inputting that code or number on the other device. A disadvantage of such a method is that the code must be stuck, via a sticker, onto the device which is both time consuming and a source of error in a manufacturing environment. Such a process requires quality control procedures in place and, even then, in some cases the wrong sticker may be applied to the wrong device, leading to yet further costs and time in the manufacturing process.

Another disadvantage is that such codes are usually lengthy. Therefore, input of the code on the other device is prone to user error and is time consuming.

Figure 8:
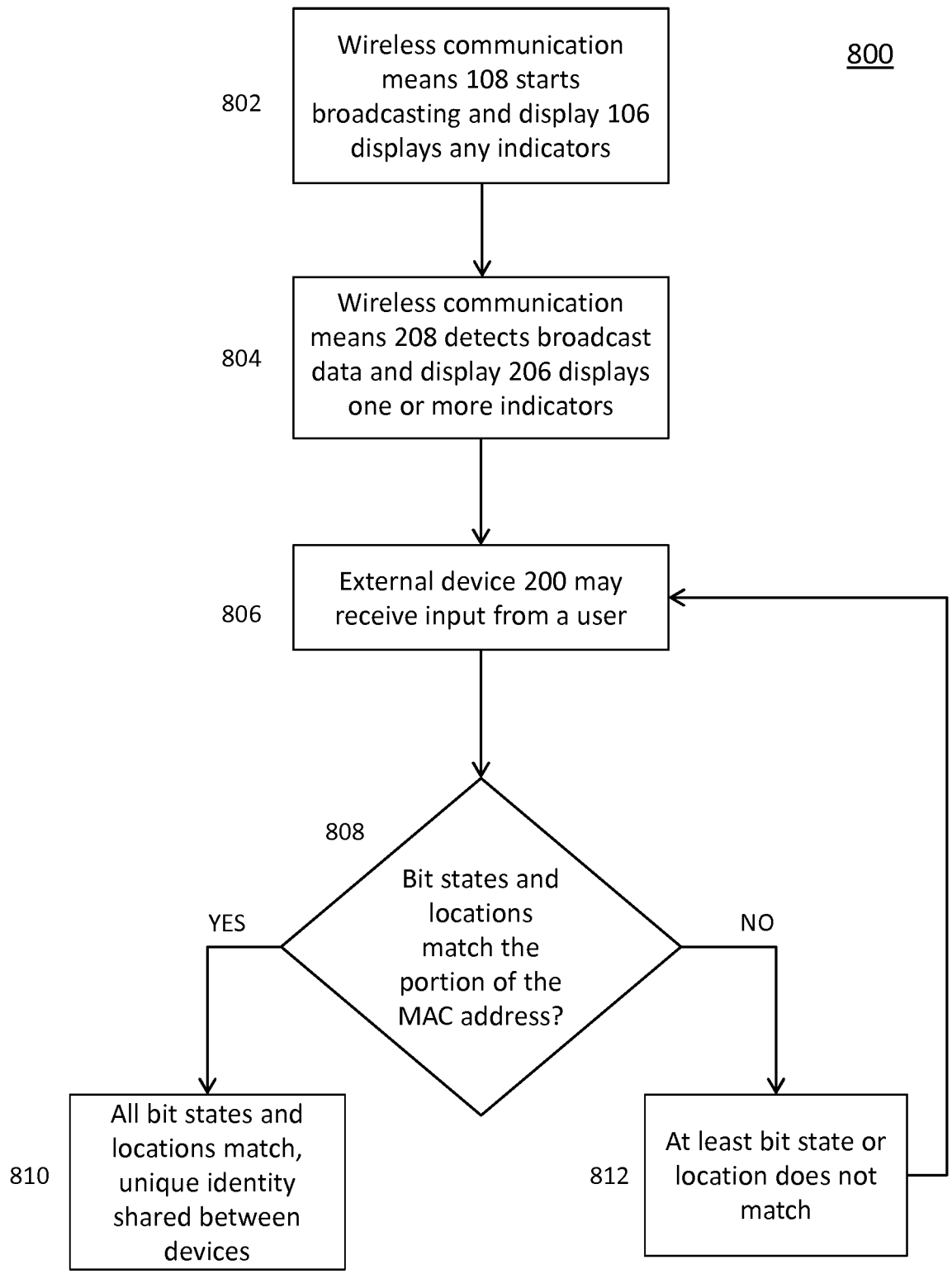
FIG. 8 shows a method of linking the testing device to a user account in accordance with an embodiment.

A method 800 of linking the testing device 100 to an external device 200 will now be described with reference to FIG. 8. As will become clear, the method 800 overcomes the above disadvantages of conventional methods by providing an efficient and cost-effective way of communicating the necessary information between the two devices, thereby providing a simple manner of linking the testing device 100 to an external device 200. The testing device 100 may be regarded as operating in a second mode in which the necessary linking steps are performed. The second mode may be termed a linking mode, and is distinct from the first, testing mode previously described in which a user uses the testing device 100 to test or read the results of a sample applied to a test stick.

The linking of the two devices is via the sharing of a unique identity. The unique identity may be a sequence of numbers, letters, symbols, alphanumeric or any combination of these that is unique to the testing device 100 or the external device 200. The steps of FIG. 8 show how the unique identity may be transmitted between the devices such that both devices have the same unique identity stored thereon. In the case that the unique identity originates from the testing device 100, the unique identity is associated with the testing device 100 and may be stored on the testing device 100 at the point of manufacture. In the case that the unique identity originals from the external device 200, the unique identity is associated with the external device 200 and may be stored on the external device 200 after specific software, such as an "app", is downloaded.

At step 802, the wireless communication means 108 of the testing device 100 is activated and starts broadcasting. In the context of Bluetooth® for example, this may be referred to as "advertising". The data broadcast by the wireless communication means 108 comprises the MAC address of the wireless communication means 108, at least part of which is represented in bits. The broadcast data may also include a device name for the testing device 100. Simultaneously or shortly after, the testing device 100 displays on the display 106 any indicators based on the mapping previously described for the testing device 100. A processor, such as a microprocessor, of the testing device 100 may be programmed to cause display of the indicators.

At this point, the memory 110 of the testing device 100 may not contain a unique identity, or may include a blank unique identity as none has been provided to the testing device 100. Alternatively, the memory 110 may contain a unique identity associated therewith at the outset for subsequent transmission to the external device 200 at step 810, as will be described.

Figure 9:
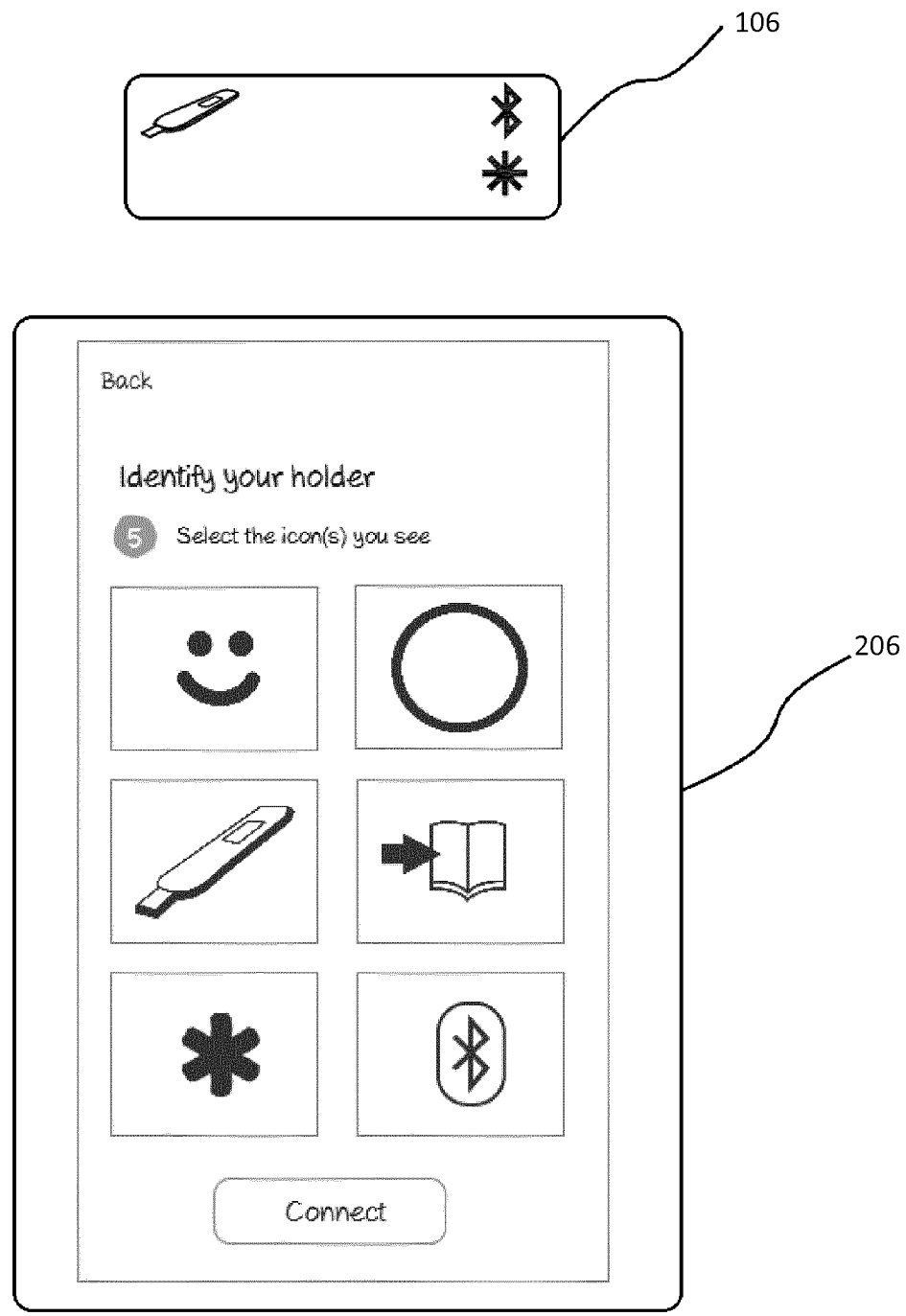
FIG. 9 shows example indicators displayed on the testing device and the external device.

Depending on the circumstances, the external device 200 may detect data broadcast from multiple devices in its vicinity. At step 804, the corresponding wireless communication means 208 of the external device 200 detects the broadcast data, including the MAC address of the wireless communication means 108. Simultaneously or shortly after, a set of indicators corresponding to those displayable by the testing device 100 is displayed on the display 206 of the external device 200. Software resident on the external device 200, such as an "app", may cause the display of the set of indicators by instructing a processor, such as a microprocessor. The set of indicators displayed on the external device 200 may be every indicator displayable by the testing device 100, or may only be a subset of the displayable indicators. While the indicators displayed on the display 206 may be in the same indicator state as those displayed on the display 106, this is not a requirement. The indicators displayed on the display 206 may therefore all be in the static state, for example. FIG. 9 shows an example of the indicators displayed on the displays 106 and 206.

Software on the external device 200 may have caused display of the indicators on the display 206 before or after the broadcast data is detected. If before, the indicators may have been displayed on running the software on the external device 200 or on selection of a specific function in the software. If after, the indicators may be displayed in response to detection of the broadcast data.

The external device 200 is capable of receiving an input from a user. At step 806, the external device 200 may receive an input selecting one or more of the indicators displayed on the display 206. The input may be via a touchscreen of the external device 200 for example, however other input means are possible. However, in the case that, on the testing device 100 and based on the mapping of the testing device 100, no indicators are displayed on the display 106, the external device 200 may receive a different input from the user or may receive no input from the user.

At step 808, in the case that the external device 200 has received the input selecting one or more indicators displayed on the display 206, the external device 200 determines whether the selected one or more indicators match the one or more indicators displayed on the display 106 of the testing device 100. This may include a determination of whether the selected indicator states also match, if appropriate. To make such a determination, the external device 200 matches the one or more selected indicators (and indicator states, if appropriate) to a bit state and a bit location value and determines whether the bit states and bit locations correspond to the portion of the MAC address. This matching is done using the mapping of the external device 200 in the same way as the mapping of the testing device 100 is used, but in reverse.

For example, if the user selects a "book" indicator on the external device 200, the external device 200 maps the "book" indicator to a corresponding bit state and bit location. As the mapping of the external device 200 includes the mapping shown in FIG. 7, the selection of the "book" indicator corresponds to the least significant bit (last bit) being in the bit state 1. As a more general example shown in FIG. 9, based on the mapping in FIG. 7, selection of only the "stick" indicator and the "star" indicator would correspond to bit 0 being 0 (No "book" indicator), bit 1 being 1 ("stick" indicator displayed), bit 2 being 0 (No "eyes and mouth" indicator) and bit 3 being 1 ("star" indicator displayed). This therefore corresponds to binary 1010. As previously mentioned, the "B" indicator may optionally always be displayed while the linking is being performed, as is shown in FIG. 9, and therefore this indicator may also be part of the selection. Optionally, selecting the "B" indicator may have no corresponding mapping unless only the "B" indicator is selected, in which case the additional mapping of the external device 200 corresponds this selection to the absence of indicators, e.g. the bits and bit states 0000.

In the case that the external device 200 does not receive the input from the user selecting one or more of the indicators displayed on the display 206, the external device matches the selection of no indicators (i.e. the absence of any indicator selection) to a bit state and bit location value, based on the mapping of the external device 200, and determines whether the bit states and bit locations correspond to the portion of the MAC address. For example, the mapping of the external device 200 may match the selection of no indicators to the portion of the MAC address being 0000. As, in this case, no input from the user selecting one or more indicators is received, the external device 200 may instead receive a different input from the user. This scenario arises in the case that the mapping of the testing device 100 results in no indicators being displayed on the display 106. Instead, the external device 200 may receive an input indicating that no selection of indicators on the display 206 is to be made. This may be by way of the user selecting no indicators and instead simply selecting a button to "proceed", for example. Alternatively, the external device 200 may not receive any input from the user, and may instead simply wait a predetermined period of time before automatically proceeding on the basis of no indicators being selected.

At step 810, if the external device 200 determines that, based on the mapping of the external device 200, the selected one or more indicators, or the absence of a selection of any indicators, matches to bit states and bit locations corresponding to the portion of the MAC address, the unique identity is transmitted between the testing device 100 and the external device 200. In other words, if the bit states and locations, based on the mapping of the external device 200, are the same as the portion of the MAC address, the unique identity is transmitted. This may be by transmitting the unique identity from the external device 200 to the device 100, or vice versa. In other words, the unique identity is shared between the two devices such that both devices now have the unique identity. The unique identity is then stored in the memory of the device receiving the unique identity.

Alternatively, at step 812, if the external device 200 determines that at least one of the selected one or more indicators does not match to a bit state or bit location corresponding to the portion of the MAC address, the method returns to step 806 to receive an input from a user. Optionally, an explanatory message may be displayed on the display 206 of the external device 200 before returning to step 806.

The sending of the unique identity between the testing device 100 and the external device 200 at step 810 establishes a link between the external device 200 and the testing device 100. Such a link provides a private connection between the two devices. In future uses, when the testing device 100 has result data or other data to transmit to the external device 200, after establishing a data connection between the two devices, the testing device 100 first requests the unique identity from the external device 200. After receiving the unique identity, the testing device 100 determines whether the received unique identity matches the unique identity stored in its memory 110. If the received unique identity matches the unique identity stored in its memory 110, the device 100 transmits the data to the external device 200 via the wireless communication means 108.

In an embodiment, the unique identity is associated with a user account. In this embodiment, the linking of the device 100 to an external device 200 involves a linking of the device 100 to the user account to which the external device 200 is or has previously "logged in". In this manner, the particular testing device 100 only communicates data to an external device 200 which is currently logged in to, or has previously logged in to, the particular user account. Software on the external device 200, such as an "app", allows a user of the external device 200 to create a personal user account in a conventional manner. For example, a username and password, along with a registration process, may be used. Once a user account is created, the unique identity associated with the user account is created or generated at an external server, and may also be stored on the external server. When or after the user has "logged in" to the user account via the app on the external device 200, the unique identity is received from the external server and also stored in the memory 210 of the external device 200. In order to link the testing device 100 and the user account, the steps of FIG. 8 are performed and the unique identity is transferred from the external device 200 logged on to the account to the testing device 100 at step 810.

Since logging in to the user account on an external device causes the external device to automatically have the unique identity associated with the specific testing device 100, different external devices may be linked to the testing device 100 purely by virtue of logging in the user account. As a result, the steps of FIG. 8 do not need to be performed more than once, even if different external devices are used to communicate with the testing device 100.

Figure 10:
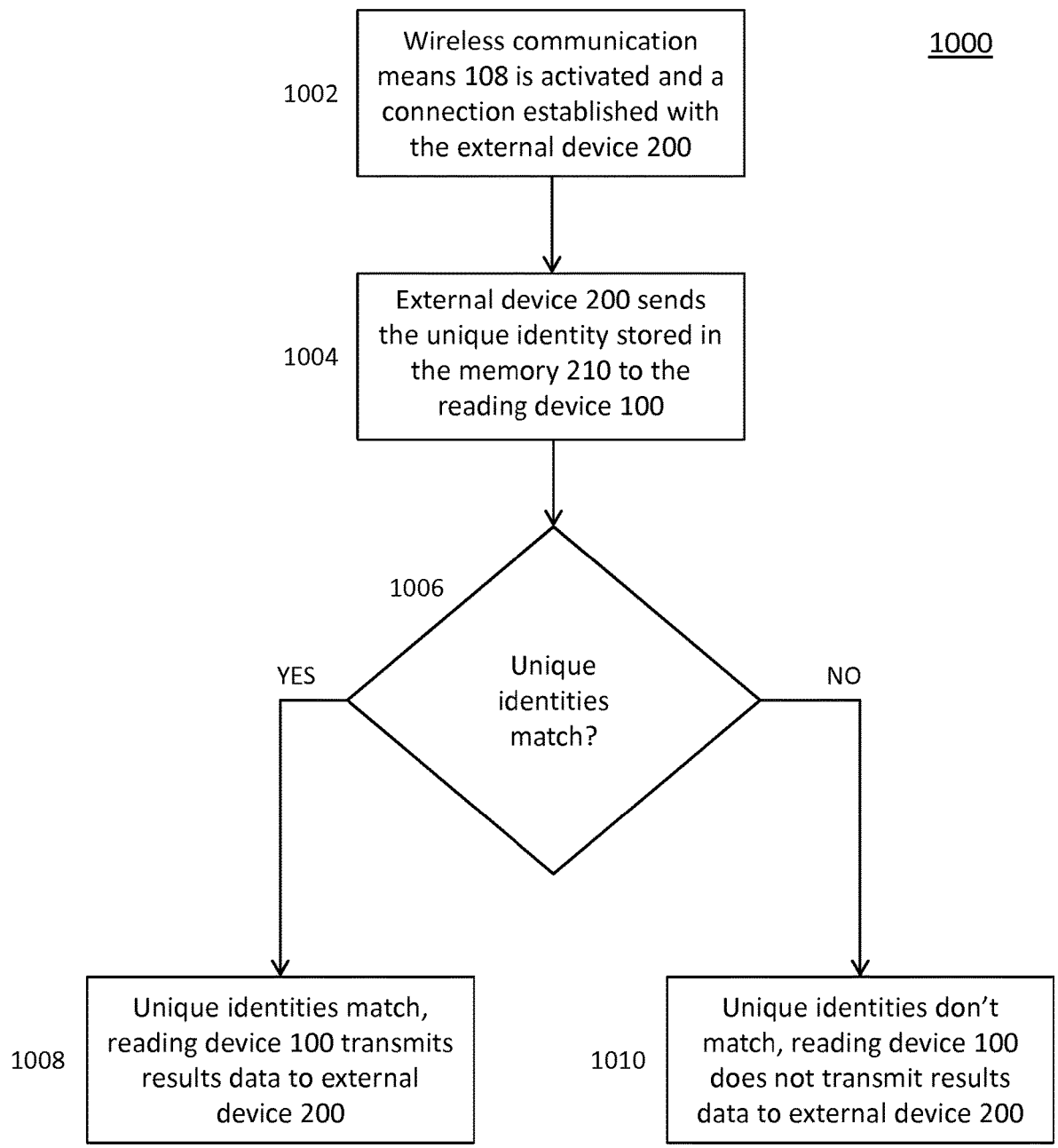
FIG. 10 shows a method of transmitting data from the testing device to the external device.

FIG. 10 shows a method 1000 of transmitting test result data from the testing device 1000 to an external device privately. At step 1002, the wireless communication means 108 of the testing device 100 is activated and a connection is established between the testing device 100 and an external device.

At step 1004, if the external device has a unique identity stored in its memory, the external device sends the unique identity to the testing device 100.

At step 1006, the testing device 100 compares the unique identity received from the external device with the unique identity stored in the memory 110 to determine whether the two unique identities match. A "match" may be defined by the two unique identities being identical, or by the two unique identities corresponding at least in part.

At step 1008, if it is determined that the unique identities match, the testing device 100 transmits results data to the external device. The transmitted results data may for example be the results of a test performed by the testing device 100.

Alternatively, at step 1010, if it is determined that the unique identities do not match, the testing device 100 does not transmit the results data to the external device.

As can be seen, the matching of indicators between the testing device 100 and an external device provides a simple and effective method of linking the testing device 100 to an external device. The transfer of test result data from the testing device 100 to an external device is only subsequently performed when the unique identities of the testing device 100 and the external device match. Additionally, the method does not require any identifier, code or number to be printed or otherwise presented on an external surface of the testing device, thereby reducing manufacturing costs and errors, and reducing the chances of possible input error. Instead, the normal functionality of the display of the testing device used in the testing mode can be beneficially repurposed to setup the link, without having to improve the display hardware. Again, this maintains a low cost to the testing device, which is particularly advantageous in the case that the testing device is designed to be disposable.

Another benefit is that, in the embodiment in which the reading device 100 is linked to a user account, as unique information (for example, the unique address) regarding the testing device is sent to an external device logged in to a user account, the specific testing device being used by a particular user can be easily identified by the manufacturer of the testing device. This is useful and important in the event that software updates need to be administered, or in the event that the testing device fails and needs to be recalled.

Aspects of the various methods described above may be implemented by a computer program product. The software resident on the testing device and the external device is an example of such a computer program product. The computer program product may include computer code arranged to instruct the devices to perform the functions of one or more of the various methods described above. The computer program and/or the code for performing such methods may be provided to an apparatus, such as the devices, on a computer readable medium or computer program product. The computer readable medium may be transitory or non-transitory. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

An apparatus such the devices may be configured in accordance with such code to perform one or more processes in accordance with the various methods discussed herein. In one arrangement the apparatus comprises a processor in additional to a memory, and a display. Typically, these are connected to a central bus structure, the display being connected via a display adapter. The devices, particularly the external device, can also comprise one or more input devices (such as a mouse and/or keyboard) and/or a communications adapter for connecting the apparatus to other apparatus or networks. In one arrangement, the database resides in the memory of the devices. Such an apparatus may take the form of a data processing system. Such a data processing system may be a distributed system. For example, such a data processing system may be distributed across a network.

The invention claimed is:

1. A method of linking a first device to a second device, the first device comprising a wireless communication means having a unique address associated therewith, the first device further comprising a display arranged to display a set of indicators, one of the first device or the second device having a unique identity stored thereon, the method comprising:
broadcasting, from the first device, the unique address;
determining, by the first device, whether one or more indicators from the set of indicators correspond to at least a portion of the unique address based on a first mapping and, if one or more indicators correspond, displaying, on the display, the corresponding one or more indicators;
detecting, by a second device, the unique address broadcast by the first device;
displaying, on the second device, the set of indicators, the second device being arranged to receive an input from a user;
wherein, if the input selects at least one indicator from the set of indicators, determining whether the selected at least one indicator corresponds to the portion of the unique address based on a second mapping; and
wherein, if the selected at least one indicator corresponds to the portion of the unique address, transmitting the unique identity between the first device and the second device.

2. The method of claim 1, wherein the unique identity is shared between the first and second devices.

3. The method of claim 1, wherein the second device has the unique identity stored thereon, the unique identity being associated with a user account.

4. The method of claim 1, wherein the first device has the unique identity stored thereon.

5. The method of claim 1, wherein the first and second mapping each comprises a list of indicators, each indicator associated with an element of the unique address.

6. The method of claim 1 wherein the display is only arranged to display indicators from the set of indicators.

7. The method of claim 1, wherein the unique address is a MAC address.

8. The method of claim 7, wherein the portion is a number of bits of the MAC address.

9. The method of claim 8, wherein the first and second mapping each comprises a list of indicators, each indicator associated with at least one bit of the MAC address.

10. The method of claim 9, wherein each indicator is associated with a bit state of at least one bit of the MAC address.

11. The method of claim 1, wherein the first device is arranged to operate in a first mode and a second mode, the first device displaying the indicators in a first indicator state while in the first mode and in a second indicator state while in the second mode, the second mode comprising the step of displaying, on the display, the corresponding one or more indicators.

12. The method of claim 11, wherein the first indicator state is different from the second indicator state.

13. The method of claim 1, wherein the first device is a result reading device, such as an ovulation test device or a pregnancy test device.

14. The method of claim 13, wherein the set of indicators comprises indicators indicative of one or more test results.

15. The method of claim 1, wherein the unique address is manufacturer specific data.

16. A system for linking a first device to second device, the system comprising a first device and a second device, one of the first device or the second device having a unique identity stored thereon, the first device comprising:

a wireless communication means having a unique address associated therewith;

a display arranged to display a set of indicators; and a memory having a first mapping stored thereon;

the second device comprising a memory having a second mapping stored thereon;

wherein the first device is arranged to:
broadcast the unique address;
determine whether one or more indicators from the set of indicators correspond to at least a portion of the unique address based on a first mapping and, if one or more indicators correspond, display the corresponding one or more indicators;

wherein the second device is arranged to:
detect the unique address broadcast by the first device;
display the set of indicators; and
receive an input from a user;

wherein the system is configured such that:
if the input selects at least one indicator from the set of indicators, the second device is further arranged to determine whether the selected at least one indicator corresponds to the portion of the unique address based on a second mapping; and if the selected at least one indicator corresponds to the portion of the unique address, the unique identity is transmitted between the first device and the second device.

17. A method of linking an external device to a user device, the method comprising:
detecting, by the user device, a unique address broadcast by the external device;
displaying, on the user device, a set of indicators, the user device being arranged to receive an input from a user;
wherein, if the input selects at least one indicator from the set of indicators, determining whether the selected at least one indicator corresponds to the portion of the unique address based on a mapping; and
wherein, if the selected at least one indicator corresponds to the portion of the unique address, transmitting a unique identity between the user device and the external device.

* * * * *